United States Patent
Dong et al.

[11] Patent Number: 5,830,502
[45] Date of Patent: Nov. 3, 1998

[54] INJECTION-MOLDED DOSAGE FORM

[75] Inventors: Liang C. Dong, Sunnyvale; Patrick S. L. Wong, Palo Alto; Crystal Pollock, Mountain View; Vincent J. Ferrari, Foster City, all of Calif.

[73] Assignee: ALZA Corporation, Palo Alto, Calif.

[21] Appl. No.: 741,752

[22] Filed: Nov. 5, 1996

Related U.S. Application Data

[63] Continuation-in-part of Ser. No. 330,892, Oct. 28, 1994, Pat. No. 5,614,578.
[51] Int. Cl.$^6$ .................................................... A61K 9/24
[52] U.S. Cl. ............................................ 424/473; 524/377
[58] Field of Search .............................. 424/473; 524/377

[56] References Cited

U.S. PATENT DOCUMENTS

| | | | |
|---|---|---|---|
| 2,799,241 | 7/1957 | Hurster | 118/24 |
| 3,845,770 | 11/1974 | Theeuwes et al. | 128/260 |
| 3,916,899 | 11/1975 | Theuwees et al. | 128/260 |
| 4,327,725 | 5/1982 | Cortese et al. | 128/260 |
| 4,855,141 | 8/1989 | Eckenhoff et al. | 424/423 |
| 5,213,809 | 5/1993 | Wright | 424/473 |
| 5,312,388 | 5/1994 | Wong | 604/892.1 |
| 5,367,003 | 11/1994 | Petcavich | 523/124 |

*Primary Examiner*—D. Gabrielle Phelan
*Attorney, Agent, or Firm*—Paul L. Sabatine; Christopher P. Rogers

[57] ABSTRACT

A dosage form is disclosed comprising an injection-molded housing member free of organic solvents.

18 Claims, 1 Drawing Sheet

INJECTION-MOLDED DOSAGE FORM

CROSS-REFERENCE TO RELATED APPLICATIONS

This application is a continuation-in-part of U.S. application Ser. No. 08/330,892 filed Oct. 28, 1994, now U.S. Pat. No. 5,614,578 issued Mar. 25,1997

FIELD OF THE INVENTION

This invention pertains to dosage forms provided by injection-molded principles. More specifically, the invention relates to injection-molded membranes manufactured into advanced dosage forms especially for the oral administration of a therapeutic agent. The invention concerns also compositions comprising at least one polymer used for injection-molding into an article of manufacture.

BACKGROUND OF THE INVENTION

Unique dosage forms, manufactured as delivery systems entered the fields of medicine and pharmacy with the invention of delivery systems by inventors Theeuwes and Higuchi as disclosed in U.S. Pat. Nos. 3,845,770 and 3,916, 899. The delivery systems disclosed in these patents comprise a rate-controlling membrane that surrounds a compartment containing a therapeutic agent. The rate-controlling membrane is permeable to the passage of an external fluid, and it is substantially impermeable to the passage of drug. There is at least one exit through the membrane for delivering the therapeutic agent from the dosage form.

A pioneering advancement in delivery systems in the dispensing arts was presented in U.S. Pat. No. 4,327,725 by patentees Cortese and Theeuwes. This invention provides a delivery system for delivering a therapeutic agent that, because of its solubility in aqueous and biological fluids is difficult to deliver in meaningful amounts at a controlled rate over time. The delivery system of this patent comprises a semipermeable wall that surrounds a compartment containing a therapeutic agent that is insoluble to very soluble in aqueous and biological fluids, and an expandable hydrogel. In operation, the hydrogel expands in the presence of an external fluid that is imbibed into the delivery system and pushes the therapeutic agent from the delivery system through an exit passageway.

A further contribution to the delivery arts is an inventive delivery system disclosed in U.S. Pat. No. 5,023,088 by patentees Wong, Theeuwes, Eckenhoff, Larsen, and Huynh. In this patent, the patentees disclosed a delivery system that comprises a semipermeable housing member with a compartment that contains a plurality of movable therapeutic units. The patentees disclosed further a driving member for displacing the therapeutic units through an opened orifice formed in the housing members, when the delivery system is in operation in an environment of use.

It will be appreciated by those skilled in the dispensing art, that the above disclosed dosage forms have a positive, inventive value, and they represent a practical and useful advancement in the dispensing art. Also, while the above described dosage forms possess ideal kinetics useful for delivering numerous and different drugs at a controlled and continuous rate to many environments of use, there is an instance where the manufacture of these dosage forms can be improved to lead to more desirable results. For example, the dosage forms of the prior art are manufactured by a process of membrane coating wherein an organic solvent, such as acetone or methylene chloride, is used to coat the membrane onto the dosage form. While these solvents form excellent membranes, there are serious shortcomings associated with their use. That is, these organic solvents are expensive, they are explosive, traces can be possibly toxic, and during processing solvent 30 fumes can escape and cause environmental concern. The conditions needed for optimizing production to produce a thin or a thick membrane often become impractical in mass production as variability between membrane weight and thickness uniformity can lead to differences in release profiles of the dosage form. Further, the optimization of coating conditions are very costly of each successive layer scale and production of a thick membrane often becomes impractical in mass production due to extremely long coating time. In addition, some special shapes of membrane could not be fabricated by the prior art coating process because of this complex geometric shape.

It will be appreciated by those skilled in the dispensing art, that if a dosage form can be provided that exhibits a high level of reliable dispensing activity and is manufactured by a process that overcomes the shortcomings and disadvantages associated with the prior art, such a dosage form and its accompanying manufacturing process would have a positive value and also represent an advancement in the dispensing art. It will be immediately appreciated also by those skilled in the dispensing art that as a dosage form designed as an osmotic essentially free from organic solvents, such a dosage form would find a practical application in the fields of pharmacy and medicine. Likewise, it will be appreciated by those skilled in the art that if a novel composition is provided for injection-molding that lessens the problems known heretofore, such a composition would represent a positive advancement in the art.

OBJECTS OF THE INVENTION

Accordingly, in view of the above presentation, it is an immediate object of this invention to provide a dosage form designed for therapy that can be manufactured by manufacturing techniques that overcome the shortcomings and disadvantages known to the prior art.

Another object of the invention is to provide a dosage form designed and manufactured essentially-free of organic solvents.

Another object of the invention is to provide an injection-molding process for manufacturing membranes for dosage forms that can be used in mass commercial production.

Another object of the invention is to provide membranes made by an injection-molding procedure wherein the membrane possesses permeability to water, is substantially impermeable to a therapeutic agent, and possesses mechanical properties useful for manufacturing an osmotic dosage form.

Another object of the invention is to provide a composition useful for injection-molding items of medicine and health.

Another object of the invention is to provide a composition with thermoplastic properties.

Another object of the invention is to provide a composition comprising at least one polymer, which composition is capable of being injection-molded into any desired shape, preferably as a housing member for a dosage form.

Another object of the invention is to provide a composition comprising two or more polymers useful for thermoplastic-molding thereof.

Other objects, features, aspects, and advantages of this invention will be more apparent to those versed in the dispensing art from the following detailed specification taken in conjunction with the accompanying claims.

DETAILED DESCRIPTION OF THE INVENTION

According to the mode and manner of this invention, novel compositions are provided for injection-molding into membranes, that are shaped into dosage forms. The compositions comprise a thermoplastic polymer, or copolymer, or the compositions comprise a mixture of thermoplastic polymers and optional injection-molding ingredients. The thermoplastic polymer that can be used for the present purpose comprise polymers that have a low softening point, for example, below 200° C., preferably within the range of 40° C. to 180° C. The polymers are preferably synthetic resins, for example, linear polycondensation resins, condensation polymerized resins, addition polymerized resins, such as polyamides, resins obtained from diepoxides and primary alkanolamines, resins of glycerine and phthalic anhydrides, polyvinyl resins, polymer resins with end-positions free or esterified carboxyl or carboxamide groups, for example with acrylic acid, acrylic amide, or acrylic acid esters, polycaprolactone, and its copolymers with dilactide, diglycolide, valerolactone and decalactone, a resin composition comprising polycaprolactone and polyalkylene oxide, composition comprising polycaprolactone and a polyalkylene oxide such as polyethylene oxide, cellulose such as hydroxypropylmethylcellulose, hydroxyethylmethylcellulose, hydroxyethylcellulose, and hydroxypropylcellulose, copoly(butylene terephthalate-tetrahydrofuran), copoly(alkylene oxide-methylmethacrylate), and ethylene vinylacetate copolymer. The membrane forming composition can comprise optional membrane-forming ingredients such as polyethylene glycol, talcum, polyvinylalcohol, lactose, or polyvinyl pyrrolidone. The compositions for forming an injection-molding polymer composition can comprise 100% thermoplastic polymer. The composition in another embodiment comprises 10% to 99% of a thermoplastic polymer, and 1% to 90% of a different polymer with the total equal to 100%. The invention provides also a thermoplastic polymer composition comprising 1% to 98% of a first thermoplastic polymer, 1% to 90% of a different, second polymer, and 1% to 90% of a different, third polymer, with all polymers equal to 100%.

Representative compositions provided by the invention comprise 20% to 90% of thermoplastic polycaprolactone and 10% to 80% of poly(alkylene oxide); a composition comprising 20% to 90% polycaprolactone and 10% to 60% of poly(ethylene oxide) with the ingredients equal to 100%; a composition comprising 10% to 97% polycaprolactone, 10% to 97% poly(alkylene oxide), and 1% to 97% of poly(ethylene glycol) with all ingredients equal to 100%; a composition comprising 10% to 90% polycaprolactone, 10% to 80% polyalkylene glycol and 1% to 40% poly(ethylene glycol-co-propylene glycol) with all ingredients equal to 100%; a composition comprising 20% to 90% polycaprolactone and 10% to 80% of hydroxypropylcellulose with all ingredients equal to 100%; a composition comprising 1% to 90% polycaprolactone, 1% to 90% poly(ethylene oxide), 1% to 90% hydroxypropylcellulose and 1% to 90% poly(ethylene glycol) with all ingredients equal to 100%; 10% to 90% caprolactone-lactide copolymer and 10% to 80% poly(ethylene oxide) with all polymers equal to 100%; 10% to 90% caprolactone-glycolide and 10% to 80% poly(ethylene oxide) with all polymer materials equal to 100%; and 10% to 90% copoly(terephthalate-tetramethylene glycol) and 10% to 80% ethylene vinylacetate with all polymer components equal to 100%. The percent (%) expressed is weight percent (wt %).

In another embodiment of the invention, a composition for injection-molding to provide a membrane is prepared by blending a composition comprising a polycaprolactone of 63 wt %, a polyethylene oxide of 27 wt %, and a polyethylene glycol of 10 wt % in a conventional mixing machine, such as a Moriyama® Mixer at 65° C. to 95° C., with the ingredients added to the mixer in the following addition sequence: polycaprolactone, polyethylene oxide and polyethylene glycol. All the ingredients were mixed for 135 minutes at a rotor speed of 10 to 20 rpm. Next, the blend is fed to a Baker Perkins Kneader® extruder at a 80° C. to 90° C., at a pump speed of 10 rpm and a screw speed of 22 rpm, and then cooled to 10° C. to 12° C. to reach a uniform temperature. Then, the cooled extruded composition is fed to an Albe pelletizer, converted into pellets at 25° C. and a length of 5 mm. The pellets next are fed into an injection-molding machine, an Arburg Allrounder® at 200° F. to 350° F. (93° C. to 177° C.), heated to a molten polymeric composition, and the liquid polymer composition forced into a mold cavity at high pressure and speed until the mold is filled and the composition comprising the polymers are solidified into a preselected shape. The parameters for the injection-molding consists of a band temperature through zone 1 to zone 5 of the barrel of 195° F. (91° C) to 375° F. (191° C.), an injection-molding pressure of 1818 bar, a speed of 55 $cm^3/s$, and a mold temperature of 75° C.

The phrase therapeutic agent and drug are used interchangeably herein, and they refer to an agent, drug compound, composition of matter or mixture thereof which provides a therapeutic or beneficial effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles, zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system, and the central nervous system. Suitable agents may be selected from, for example, proteins, enzymes, hormones, polynucleotides, nucleoproteins, polysaccharides, glycoproteins, M. lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents which this invention can be utilized with are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproterenol sulfate, phenmetrazine sulfate, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydroxycorticosterone acetate, cortisone acetate, dexamethasone and its derivatives such as betamethasone, triamcinolone, methyltestosterone, 17-b-estradiol, ethinyl estradiol, ethinyl estradiol 3-methyl ether, prednisolone, 17-b-hydroxyprogesterone acetate, 19-norprogesterone, norgestrel, norethindrone, norethisterone, norethiederone, progesterone, norgesterone, norethisterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, mandol, quabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, endlapriat, famotidine, nizatidine, sucralfate, etintidine, tertatolol, minoxidil, chlordiazepoxide, diazepam, amitriptyline, and imipramine. Further examples are proteins and protein-related compounds which include, but are not limited to, peptides, insulin, protease inhibitors such as indinivar, ritonavir, saquinavir, nelfinavir, VX-478 and SC-52151, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one therapeutic agent can be incorporated into the dosage form of this invention, and the use of the expressions therapeutic agent or drug in no way excludes the use of two or more such therapeutic agents or drugs. The therapeutic agent can be in a wide variety of chemical and physical forms, such as uncharged molecules, components of molecular complexes, nonirritating pharmaceutically acceptable salts, therapeutic derivatives of the therapeutic agent such as ethers, esters, amides, etc, therapeutic derivatives of the therapeutic agent that are easily hydrolyzed by the body pH, and enzymes, are included in this invention. The amount of therapeutic agent in the dosage form is an amount necessary to produce the desired therapeutic response. In practice, this will vary widely depending upon the particular therapeutic agent, the site of delivery, the severity of the medical condition, and the desired therapeutic effect. Thus, often it is not practical to define a particular therapeutic range for a therapeutically effective dose of the therapeutic active agent incorporated into the dosage form, however, the dosage form generally will contain 10 ng to 1.5 g of the therapeutic agent delivered at the rate of 0.4 ng to 65 mg per hour over 24 hours. The therapeutically active drugs are disclosed in *Pharmacotherapy*, Vol. 8, pp. 147–157 (1988); *Drugs*, Vol. 30, pp. 333–354 (1985); *Remington's Pharmacological Basis of Therapeutics* by Goodman and Gilman, 4th Ed. (1970) published by The Macmillan Company, London.

The term osmagent as used herein also includes osmotically effective solute, osmotically effective compound and osmotic agent. The osmotically effective compounds that can be used for the purpose of this invention include inorganic and organic compounds that exhibit an osmotic pressure gradient across a semipermeable membrane against an external fluid. Osmotically effective compounds useful for the present purpose include magnesium sulfate, magnesium chloride, sodium chloride, lithium chloride, potassium sulfate, sodium carbonate, sodium sulfate, lithium sulfate, potassium chloride, calcium bicarbonate, calcium sulfate, potassium acid phosphate, calcium lactate, mannitol, urea, inositol, magnesium succinate, tartaric acid, carbohydrates, raffinose, sucrose, glucose, lactose monohydrate, and mixtures thereof. The osmotically effective solute can be in any physical form such as particle, crystal, pellet, tablet, strip, ground, pulverized, film, or granules. The osmotically effective solutes and procedures for measuring osmotic pressures are disclosed in U.S. Pat. No. 5,232,705.

The push composition contains an expandable means also known as osmopolymer, hydrogel, and expandable member in the dosage form for the purpose of this invention comprise a push composition that interacts with water, or aqueous biological fluids and swell or expand to an equilibrium state. The osmopolymers exhibit the ability to swell in water and retain a significant portion of the imbibed water within the polymer structure. The osmopolymers that can be used in the second layer swell or expand to a very high degree, usually exhibiting a 2 to 50 fold volume increase. The osmopolymers can be noncrosslinked or crosslinked. The swellable, hydrophilic polymers are, in one presently preferred embodiment, lightly crosslinked, such as cross-links being formed by covalent or ionic bonds. The osmopolymers can be of plant, animal or synthetic origin. Hydrophilic polymers suitable for the present purpose include poly (hydroxyalkylmethacrylate) having a number-average molecular weight of from 30,000 to 5,000,000; poly (vinylpyrrolidone) having a viscosity-average molecular weight of from 10,000 to 360,000; anionic and cationic hydrogels; polyelectrolyte complexes; poly(vinyl alcohol) having a low acetate residual, crosslinked with formaldehyde, or glutaraldehyde and having a degree of polymerization from 200 to 30,000; a mixture of methyl cellulose, crosslinked agar and carboxymethyl cellulose, a water insoluble, water swellable copolymer produced by forming a dispersion of finely divided copolymer of maleic anhydride with styrene, ethylene, propylene, butylene or isobutylene crosslinked with from 0.0001 to about 0.5 moles of polyunsaturated crosslinking agent per mole of maleic anhydride in the copolymer; water swellable polymers of N-vinyl lactams, and the like.

Other osmopolymers for providing the push layer include polymers that form hydrogels such as Carbopol® acidic carboxy polymers generally having a number-average molecular weight of 450,000 to 4,000,000; the sodium salt of Carbopol® acidic carboxy polymers and other metal salts; Cyanamer® polyacrylamides; crosslinked water swellable indene maleic anhydride polymers; Goodrite® polyacrylic acid having, but not limited to, a number-average molecular weight of 80,000 to 200,000, and the sodium and other metal salts; Polyox® polyethylene oxide polymers having, a weight-average molecular weight of 100,000 to 7,800,000; sodium carboxymethylcellulose of 1,500,000 to 5,000,000 weight-average molecular weight; starch graft copolymers; Aqua-Keeps® acrylate polymers; diester crosslinked polyglucan, polyethylene glycol of 1050 to 50,000 viscosity-average molecular weight, and the like. Representative polymers that form hydrogels are known to the prior art in U.S. Pat. No. 3,865,108 issued to Hartop; U.S. Pat. No. 4,207,893 issued to Michaels, and in *Handbook of Common Polymers*, by Scott and Roff, CRC Press, Cleveland, Ohio.

Other osmopolymers that can be present in the first layer include agarose, alginates, amylopectin, arabinoglactan, carrageen, eucheuma, fucoidan, furcellaran, gelatin, guar gum, gum agar, gum arabic, gum ghatti, gum karaya, gum tragacanth, hypnea, laminarin, locust bean gum, pectin, polyvinyl alcohol, polyvinyl pyrrolidone, propylene glycol aginates, N-vinyl lactam polysaccharides, xanthan gum, poly(ethylene oxide) of 75,000 to 350,000 weight-average molecular weight, and the like. The osmopolymers are known in *Controlled Release Systems: Fabrication Technology*, Vol. 11, p. 46 (1988) CRC Press.

The compositions comprising a therapeutic agent for use in the invention are made by standard manufacturing techniques. For example, in one manufacture, a therapeutic agent is mixed with composition forming ingredients and then pressed into a solid shape corresponding to the internal dimensions of the space inside the dosage form. In another manufacture, the therapeutic agent and other composition forming ingredients are mixed into a solid, or into a semisolid, by conventional methods such as balimilling, calendering, stirring, or rollmilling, and then pressed into a preselected layer forming shape. A push expansion composition comprising an osmopolymer-hydrogel is prepared in a similar manner, and pressed into a shape corresponding to the internal composition of the dosage form. Procedures for preparing a therapeutic agent composition, and an osmopolymer-hydrogel composition are disclosed in U.S. Pat. No. 5,024,843.

EXAMPLES

The following examples are illustrative of the present invention, and they should not be considered as limiting the scope of the invention in any way as these examples and other equivalents thereof will become apparent to those versed in the art in light of the present disclosure and the accompanying claims.

A dosage form comprising an injection-molded membrane consisting of the polycaprolactone, polyethylene oxide and polyethylene glycol composition that surrounds an internal space with an opened mouth and a closed bottom is charged at its bottom with a push composition and then with a drug composition at the opened mouth. The push composition comprises 58.75 wt % sodium carboxymethylcellulose of 2,500,000 weight-average molecular weight, 30.00 wt % sodium chloride, 5.00 wt % hydroxypropylmethylcellulose of 9,200 number-average molecular weight, 5.00 wt % hydroxypropylcellulose of 20,000 number-average molecular weight, 1.00 wt % red ferric oxide, and 0.25 wt % magnesium stearate. The drug composition comprises 66.70 wt % gemfibrozil, 14.30 wt % acid-di-sol, a sodium croscarmellose, 9.50 wt % polyethylene oxide of 200,000 weight-average molecular weight, 5.00 wt % Myrj 52-S surfactant, also known as poly(ethylene glycolate 40) stearate, 3.00 wt % hydroxypropylmethylcellulose of 9,200 number-average molecular weight, 1.00 wt % cab-O-sil, a colloidal silicon dioxide, and 0.50 wt % magnesium stearate. The opened mouth of the dosage form is crimped to 155 mil (3.94 mm) orifice to provide an osmotic dosage form. A prior art dosage form made by solvent technique is disclosed in U.S. Pat. No. 4,327,725, issued to Cortese and Theeuwes, and assigned to the ALZA Corporation.

Another dosage form provided by the invention comprises a housing consisting of a first membrane section and a second membrane section. The first section and the second section are designed to close in telescopic arrangement with each other. The membrane forming the first section is injection-molded from a polycaprolactone or ethylene vinyl acetate copolymers, and the second section comprises polycaprolactone, polyethylene oxide and polyethylene glycol at various ratios. The first section comprises a therapeutic composition for administering to an animal or to a human. The second section is a means for closing the first section as a cap during storage. The second section is a means for opening the dosage form, when the dosage form is in operation in a fluid environment of use for dispensing a therapeutic composition from the first section to the environment. The second section comprises an osmotic layer comprising 58.75 wt % sodium carboxymethylcellulose of 2,500,000 weight-average molecular weight, 30.00 wt % sodium chloride, 5.00 wt % hydroxypropylmethylcellulose of 9,200 number-average molecular weight, 5.00 wt % hydroxypropylcellulose of 20,000 number-average molecular weight, 1.00 wt % red ferric oxide, and 0.25 wt % magnesium stearate. The osmotic layer is positioned against the bottom of the second section. Next, a barrier layer comprising 95.00 wt % stearic acid and 5.00 wt % hydroxypropylmethylcellulose of 9,200 number-average molecular weight is positioned on the section in bilayer arrangement with the osmotic layer. The dosage form is assembled by the smaller opened end fitted inside the layer open end and compressed together until the first section and the second section fit together tightly. A dosage form made by solvent techniques is disclosed in U.S. Pat. No. 5,312,388 issued to Wong, Theeuwes, and Larsen, and assigned to the ALZA Corporation. Conventional injection-molding machines as disclosed in *Encyclopedia of Polymer Science and Engineering*, Vol. 8, Injection-Molding, pp.102–138 (1987) can be used for the purpose of this invention.

A dosage form is manufactured for containing a liquid formulation by injection-molding a housing member for containing the liquid formulation. The housing member comprises a semipermeable membrane that surrounds an internal compartment. The housing has a wide opened mouth and a closed bottom. The injection-molded membrane comprises a polycaprolactone and a cellulose derivative blend or polycaprolactone, polyethylene oxide and polyethylene glycol to provide a semipermeable membrane. The cellulose derivative is selected from the group consisting of a cellulose ether, cellulose ester, hydroxyalkylcellulose and hydroxypropylalkylcellulose. The dosage form is manufactured by first placing in the bottom of the housing an expandable-push pressed layer comprising 79.00 wt % Keltone HV, sodium alginate, 15.00 wt % calcium sulfate, 5.00 wt % poly(vinylpyrrolidone), 0.50 wt % ferric oxide, and 0.50 wt % magnesium stearate; next a barrier layer for preventing a liquid formulation from mixing with the expandable-push layer is inserted into the opened housing member in contacting bilayer arrangement. The barrier layer comprises 95.00 wt % stearic acid and 5.00 wt % hydroxypropylmethylcellulose. Next, membrane surrounding the opened mouth is crimped against air pressure leaving an orifice of 30 mil. A liquid formulation then is injected into the crimped housing member through the orifice. The liquid formulation comprises 41.75 wt % cremophor, a polyoxyl 40 hydrogenated castor oil, 35.05 wt % corn oil, 21.97 wt % propylene glycol, 1.10 wt % tocopherol, and 0.14 wt % blue dye.

The procedures disclosed supra are followed to provide a dosage form for delivering a therapeutic composition to a human patient in need of therapy. The dosage form comprises an injection-molded polymeric membrane that surrounds an internal space, is closed at one end and open at the distant end. The internal space is filled with a therapeutic composition, the open end closed after the internal space is filled with the therapeutic composition, and then a passageway is laser drilled through the closed membrane to provide an exit passageway for delivering the therapeutic composition to the patient. The polymeric compositions used for providing the injection-molded membrane comprise: (a) 10% to 90% caprolactone-lactide copolymer and 10% to 80% poly(alkylene oxide); (b) 10% to 90% caprolactone-glycolic copolymer and 10% to 90% poly(alkylene oxide); (c) 10% to 90% caprolactone-lactide, 10% to 50% poly (alkylene oxide) and 10% to 50% poly (hydroxyalkylcellulose) wherein the alkyl is selected from the group consisting of methyl, ethyl, propyl and butyl; (d) 20% to 90% polycaprolactone and 10% to 80% ethylene-vinylacetate copolymer; (e) 10% to 90% terephthalate-tetramethylene glycol copolymer and 10% to 40% ethylene vinylacetate copolymer; and (f) 20% to 70% polycaprolactone and 10% to 60% copoly(alkylene oxide methylmethacrylate); and (g) 20% to 85% polycaprolactone and 10% to 65% terephthalate-vinylacetate copolymer; with all injection-molding compositions equal to 100 wt %.

BRIEF DESCRIPTION OF THE DRAWINGS

Accompanying FIGS. 1 and 2, demonstrate the unexpected properties provided by the invention.

Figure 1:
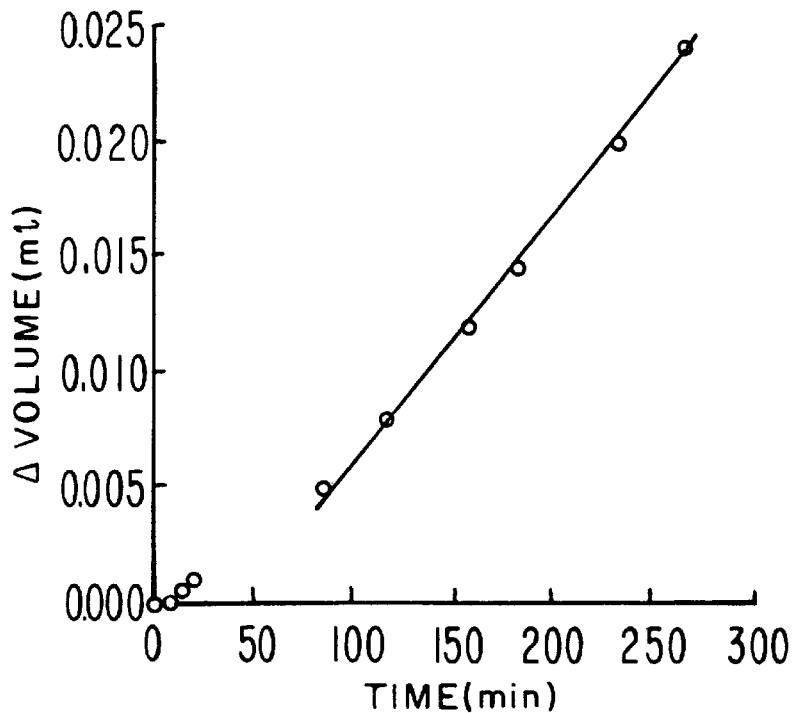
In FIG. 1, the permeability of a membrane comprising 63 wt % polycaprolactone, 27 wt % polyethylene oxide of 5,000,000 molecular weight and 10 wt % polyethylene glycol 3350 is expressed as volume against time. The water permeation through the membrane was measured with a saturated salt solution having an osmotic pressure (P) for a membrane of 20 mils thick (0.5/mm), at a temperature of 37° C., and a permeability area of 0.64 cm². The permeability equation used is as follows: K(cm mil/hr. atm)=1·(dV/dt)/(A·P), wherein dV/dt equals the slope of the v vs. t (volume vs. time) plot, l equals the thickness of membrane, A equals permeation area, and P equals the osmotic pressure of the salt solution. Accompanying
Figure 2:
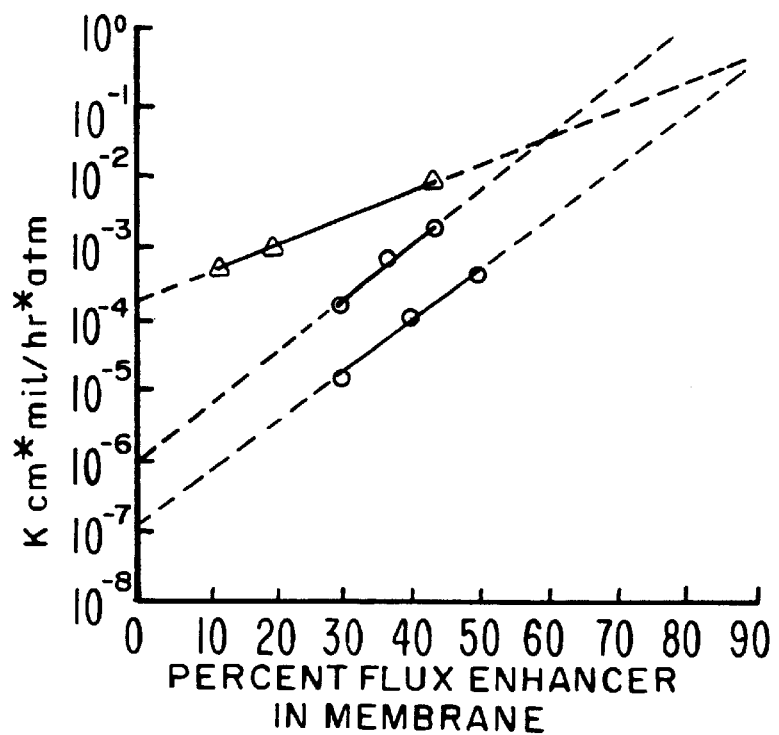
FIG. 2 illustrates the permeability through membranes of various compositions. In the drawing FIG. 2, the clear triangle illustrates the aqueous permeability through a cellulose acetate membrane comprising an acetyl content of 39.8% at changing percents of polyethylene glycol flux enhancer in coated membranes; the clear circles depict the aqueous flux through a membrane comprising polycaprolactone and polyethylene oxide of 5,000,000 molecular weight at a ratio of 70/30 with additional amounts of polyethylene glycol 3350; and the black circles denote the effect of varying concentration of flux enhancer on the water permeability through a polycaprolactone—hydroxypropylcellulose calendered membranes.

Inasmuch as the foregoing specification comprises preferred embodiments of the invention, it is understood that variations and modifications may be made herein, in accordance with the inventive principles disclosed, without departing from the scope of the invention.

We claim:

1. A dosage form for delivering a therapeutic agent to an environment of use, the dosage form comprising:
    (a) an internal compartment;
    (b) a therapeutic composition comprising a therapeutic agent in the compartment;
    (c) an expandable composition comprising means for pushing the therapeutic composition from the dosage form in the compartment;
    (d) exit means in the dosage form that connects the therapeutic composition with the environment of use, and wherein the dosage form comprises:
    (e) an injection-molded membrane comprising a thermoplastic polycaprolactone, which injection-molded membrane is permeable to the passage of fluid and surrounds, defines and forms the internal compartment.

2. The dosage form for delivering the therapeutic agent according to claim 1; wherein the injection-molded membrane comprises a polycaprolactone copolymer with a member selected from the group consisting of dilactide, diglycolide, valerolactone and decalactone.

3. The dosage form for delivering the therapeutic agent according to claim 1, wherein the injection-molded membrane comprises a polycaprolactone and a polyalkylene oxide.

4. The dosage form for delivering the therapeutic agent according to claim 1, wherein the injection-molded membrane comprises polycaprolactone, polyalkylene oxide and poly(ethylene glycol-co-propylene glycol).

5. The dosage form for delivering the therapeutic agent according to claim 1, wherein the injection-molded membrane comprises a polycaprolactone and polyethylene glycol.

6. A dosage form for delivering a therapeutic agent to an environment of use, wherein the dosage form comprises:
    (a) a first section;
    (b) a second section;
    (c) an internal lumen formed by the first section and the second section;
    (d) a therapeutic composition in the first section;
    (e) an osmotic composition in the second section; and wherein the dosage form comprises;
    (f) an injection-molded membrane, used for forming the first section and the second section, which membrane defines the first and second sections that form the internal lumen, the injection-molded membrane comprising a softening temperature of 40° C. to 180° C. and is permeable to the passage of fluid in the environment of use.

7. A dosage form for delivering a therapeutic agent to an environment of use, wherein the dosage form comprises:
(a) a first section;
(b) a second section;
(c) an internal lumen formed by the first section and the second section;
(d) a therapeutic composition in the first section;
(e) an osmotic composition in the second section comprises;
(f) an injection-molded thermoplastic membrane forming the first section and the second section, the injection-molded membrane comprising a polycaprolactone that is permeable to the passage of fluid.

8. The dosage form for delivering the therapeutic agent according to claim 7, wherein the injection-molded membrane comprises a polycaprolactone copolymer selected from the group consisting of polycaprolactone dilactide copolymer, polycaprolactone diglycolide, polycaprolactone valerolactone, and polycaprolactone decalactone.

9. A dosage form for delivering a therapeutic agent to an environment of use, wherein the dosage form comprises:
(a) a first section;
(b) a second section;
(c) an internal lumen formed by the first section and the second section;
(d) a therapeutic composition in the first section;
(e) an osmotic composition in the second section; and wherein the dosage form comprises:
(f) an injection-molded thermoplastic membrane forming the first section and the second section, the injection-molded membrane comprising a polycaprolactone and a polyalkylene oxide.

10. A dosage form for delivering a therapeutic agent to an environment of use, wherein the dosage form comprises:
(a) a first section;
(b) a second section;
(c) an internal lumen formed by the first section and the second section;
(d) a therapeutic composition in the first section;
(e) an osmotic composition in the second section and wherein the dosage form comprises:
(f) an injection-molded thermoplastic membrane forming the first section and the second section, the injection-molded membrane comprising a polycaprolactone, polyalkylene oxide and poly (ethylene glycol-co-propylene glycol).

11. A dosage form for delivering a therapeutic agent to an environment of use, wherein the dosage form comprises:
(a) a first section;
(b) a second section;
(c) an internal lumen formed by the first section and the second section;
(d) a therapeutic composition in the first section;
(e) a composition comprising an osmopolymer in the second section comprises:
(f) an injection-molded thermoplastic membrane forming the first section and the second section that comprises a polycaprolactone and a polyalkylene glycol.

12. A dosage form for delivering a therapeutic liquid formulation to an environment of use, wherein the dosage form comprises:
(a) an internal compartment;
(b) an exit in the dosage form that connects the internal compartment with the environment of use;
(c) an osmotic composition in the internal compartment distant from the exit; and wherein the dosage form comprises:
(d) a therapeutic liquid formulation in the internal compartment and adjacent to the exit; and,
(e) an injection-molded thermoplastic membrane comprising a softening temperature of 40° C. and 180° C. that surrounds and forms the internal compartment, the injection-molded membrane permeable to the passage of fluid in the environment of use.

13. A composition comprising 10% to 90% caprolactone-lactide copolymer and 10% to 80% of polyalkylene oxide with the composition equal to 100% and used for injection-molding a polymer membrane.

14. A composition comprising 10% to 90% caprolactone-glycolide copolymer and 10% to 90% polyethylene oxide with the composition equal to 100% and used for injection-molding a polymer membrane.

15. A composition comprising 10% to 90% caprolactone-lactide copolymer, 10% to 50% polyethylene oxide and 10% to 50% poly(ethylene glycol-co-propylene glycol) with the composition equal to 100% and used for injection-molding a polymer membrane for manufacturing on oral dosage form.

16. A composition comprising 20% to 90% polycaprolactone and 10% to 80% ethylene-vinylacetate copolymer with the composition equal to 100% and the composition used for injection-molding a polymer membrane for manufacturing a therapeutic dosage form.

17. A process for manufacturing a dosage form, wherein the process comprises:
(a) injection molding a membrane into a shape that surrounds an internal space, which space comprises an opened end and a closed end;
(b) placing in the space at the closed end a composition comprising fluid imbibing properties;
(c) placing in the space at the opened end a composition comprising a drug; and
(d) closing the opened end while maintaining an exit in the end for releasing drug from the dosage form.

18. A process for providing a dosage form, wherein the process comprises:
(a) injection molding a composition comprising a polymer to provide a membrane which membrane surrounds an internal space with an opened end and a closed end;
(b) depositing in the space at the closed end a composition that expands in the presence of aqueous fluids;
(c) placing a composition comprising a drug in the space at the opened end;
(d) crimping the membrane at the opened end to close the dosage form; and
(e) maintaining an exit in the crimped end for delivering drug from the dosage form.

* * * * *